US009555224B2

United States Patent
Le

(10) Patent No.: US 9,555,224 B2
(45) Date of Patent: Jan. 31, 2017

(54) REDUCED MATERIAL TIP FOR CATHETER AND METHOD OF FORMING SAME

(71) Applicant: Abbott Cardiovascular Systems Inc., Santa Clara, CA (US)

(72) Inventor: Tram U. Le, Corona, CA (US)

(73) Assignee: ABBOTT CARDIOVASCULAR SYSTEMS INC., Santa Clara, CA (US)

(*) Notice: Subject to any disclaimer, the term of this patent is extended or adjusted under 35 U.S.C. 154(b) by 489 days.

(21) Appl. No.: 14/212,919

(22) Filed: Mar. 14, 2014

(65) Prior Publication Data

US 2014/0276400 A1 Sep. 18, 2014

Related U.S. Application Data

(60) Provisional application No. 61/800,533, filed on Mar. 15, 2013.

(51) Int. Cl.
*A61M 25/10* (2013.01)
*A61M 25/00* (2006.01)
(Continued)

(52) U.S. Cl.
CPC ....... *A61M 25/1036* (2013.01); *A61M 25/001* (2013.01); *A61M 25/0068* (2013.01); *A61M 25/1006* (2013.01); *A61M 25/1029* (2013.01); *B23K 26/36* (2013.01); *B29C 57/00* (2013.01); *A61M 2025/1093* (2013.01); *B29C 2793/00* (2013.01); *B29C 2793/009* (2013.01);
(Continued)

(58) Field of Classification Search
CPC combination set(s) only.
See application file for complete search history.

(56) References Cited

U.S. PATENT DOCUMENTS 4,661,300 A     4/1987  Daugherty
4,961,809 A  * 10/1990  Martin ................ A61M 5/1582
                                                      156/294

(Continued)

FOREIGN PATENT DOCUMENTS

EP     0 318 919 A2    6/1989
EP     0 827 758       3/1998
EP     0 850 655       7/1998

OTHER PUBLICATIONS

International Search Report and Written Opinion for PCT/US2014/028891, dated Sep. 2, 2014.

*Primary Examiner* — Benjamin Schiffman
(74) *Attorney, Agent, or Firm* — Baker Botts L.L.P.

(57) ABSTRACT

Method for fabricating a catheter including providing an inner tubular member formed from a first polymeric material, the inner tubular member having a distal section, a distal end, and a lumen defined therein by a first inner diameter; necking down at least a portion of the distal section of the inner tubular member to form a necked tip having a second inner diameter; and removing a portion of polymeric material from an inner surface along the necked tip to define a third inner diameter for the necked tip. The method can include positioning the distal section of the inner tubular member in a balloon having a working length, a distal neck, and a distal leg, with the distal end of the inner tubular member extending distally beyond a distal end of the distal leg, and coupling the distal leg of the balloon to at least a portion of the distal section of the inner tubular member.

19 Claims, 6 Drawing Sheets

(51) Int. Cl.
    *B23K 26/36*     (2014.01)
    *B29C 57/00*     (2006.01)
    *B29L 31/00*     (2006.01)

(52) U.S. Cl.
    CPC ............... *B29L 2031/7542* (2013.01); *B29L 2031/7543* (2013.01)

(56) References Cited

U.S. PATENT DOCUMENTS

| | | | |
|---|---|---|---|
| 5,240,537 A * | 8/1993 | Bodicky | A61M 25/001 156/244.13 |
| 5,360,401 A | 11/1994 | Turnland et al. | |
| 5,458,615 A | 10/1995 | Klemm et al. | |
| 5,507,768 A | 4/1996 | Lau et al. | |
| 5,718,861 A * | 2/1998 | Andrews | A61M 1/1072 264/235 |
| 5,736,085 A * | 4/1998 | Brown | A61M 25/001 264/161 |
| 5,795,521 A * | 8/1998 | Mathieu | A61M 25/001 264/163 |
| 5,843,356 A * | 12/1998 | Patel | A61M 25/001 264/161 |
| 6,217,547 B1 | 4/2001 | Lee | |
| 6,277,093 B1 | 8/2001 | Lee | |
| 6,508,966 B1 * | 1/2003 | Castro | A61M 25/0668 264/138 |
| 6,620,127 B2 | 9/2003 | Lee | |
| 6,712,833 B1 * | 3/2004 | Lee | A61M 25/1034 606/191 |
| 6,740,277 B2 * | 5/2004 | Howell | A61M 25/001 264/209.3 |
| 7,001,420 B2 | 2/2006 | Speck et al. | |
| 7,074,206 B2 | 7/2006 | Lee | |
| 7,828,766 B2 | 11/2010 | Durcan et al. | |
| 7,850,724 B2 | 12/2010 | Oliver | |
| 7,906,066 B2 | 3/2011 | Wilson et al. | |
| 7,951,259 B2 | 5/2011 | Duchamp et al. | |
| 7,967,836 B2 | 6/2011 | Warnack et al. | |
| 8,052,638 B2 | 11/2011 | Lee | |
| 8,257,420 B2 | 9/2012 | Fitzgerald et al. | |
| 8,292,913 B2 | 10/2012 | Warnack et al. | |
| 8,403,885 B2 | 3/2013 | Arana et al. | |
| 8,657,782 B2 | 2/2014 | Arana et al. | |
| 8,840,743 B2 | 9/2014 | Wantink et al. | |
| 2012/0065644 A1 | 3/2012 | Ng et al. | |
| 2012/0065718 A1 | 3/2012 | Simpson et al. | |
| 2013/0304179 A1 | 11/2013 | Bialas et al. | |
| 2013/0304181 A1 | 11/2013 | Green et al. | |

\* cited by examiner

REDUCED MATERIAL TIP FOR CATHETER AND METHOD OF FORMING SAME

CROSS-REFERENCE TO RELATED APPLICATION

This application claims priority to U.S. Provisional Patent Application Ser. No. 61/800,533, entitled "Reduced Material Tip For Balloon Catheter And Method Of Forming Same," filed Mar. 15, 2013, the contents of which are fully incorporated herein by reference.

BACKGROUND

Field

The presently disclosed subject matter relates to intraluminal catheters for use in percutaneous transluminal coronary angioplasty (PTCA) or stent delivery systems or the like. Particularly, the disclosed subject matter relates to a catheter and system having an improved distal tip.

Description of Related Art

Intraluminal catheters are well known and beneficial for a variety of medical uses, including diagnostics, therapeutics, and treatment. For example, and not limitation, balloon catheters can be used for a number of different vascular and/or coronary applications. In percutaneous transluminal coronary angioplasty (PTCA) procedures, a guidewire is typically advanced into the coronary artery until the distal end of the guidewire crosses a lesion to be dilated. A dilatation catheter having an inflatable balloon on the distal portion thereof is advanced into the coronary anatomy over the guidewire until the balloon of the dilatation catheter is properly positioned across the lesion. Once properly positioned, the dilatation balloon is inflated with inflation fluid one or more times to a predetermined size to open up the vascular passageway. Generally, the inflated diameter of the balloon is approximately the same diameter as the native diameter of the body lumen being dilated so as to complete the dilatation, but not over-expand the artery wall. After the balloon is finally deflated, blood flow resumes through the dilated artery and the dilatation catheter and the guidewire can be removed therefrom.

In addition to or as an alternative of angioplasty procedures, it can be desirable to implant an intravascular prosthesis, generally called a stent, inside the artery at the site of the lesion. Stents can also be used to repair vessels having an intimal flap or dissection or to generally strengthen a weakened section of a vessel or to maintain its patency. Stents can be delivered to a desired location within a coronary artery in a contracted condition on a balloon of a catheter, which is similar or identical in many respects to a balloon angioplasty catheter. The balloon, and thus the stent, is expanded within the patient's artery to a larger diameter. The balloon is deflated to remove the catheter with the stent implanted at the site of the dilated lesion. See for example, U.S. Pat. No. 5,507,768 (Lau et al.) and U.S. Pat. No. 5,458,615 (Klemm et al.), each of which is hereby incorporated by reference in its entirety. Alternatively, the stent can be delivered to a desired location within a coronary artery in a contracted condition under a retractable sheath of a catheter, which when pulled back allows the stent to expand within the patient's artery to a larger diameter. See for example, U.S. Pat. Nos. 5,360,401, 7,850,724, and 8,257,420 and U.S. Patent Publication Nos. 2013/0304179, 2013/0304181, and 2012/0065644, each of which is hereby incorporated by reference in its entirety.

It is desirable to provide an intraluminal catheter with a soft tip having a small entry profile to provide trackability and flexibility and to prevent or minimize injury to a vessel during advancement within the tortuous anatomy of a patient's vascular. One challenge has been forming a tip with a reduced diameter and/or thickness. For example, the tip should be thin and flexible, yet needs to be sufficiently strong to prevent guidewire lumen collapse. Accordingly, there remains a need to provide a catheter tip having a reduced diameter and/or thickness and having improved performance.

SUMMARY

In accordance with one aspect of the disclosed subject matter, a method of fabricating a catheter includes providing an inner tubular member formed from a first polymeric material. The inner tubular member has a distal section, a distal end, and a lumen defined therein by a first inner diameter. At least a portion of the distal section of the inner tubular member in necked down to form a necked tip having a second inner diameter. A portion of polymeric material is removed from an inner surface along the necked tip to define a third inner diameter for the necked tip.

As embodied herein, the second inner diameter can be less than the first inner diameter. The third inner diameter can be about equal to the first inner diameter.

For purpose of illustration, the inner tubular member can be necked down on a stepped mandrel having a first portion with a first outer diameter and a second portion having a second outer diameter, the second outer diameter being about equal to the second inner diameter. The tubular member can be necked down using a hot die having an inner diameter, wherein the necked tip has an outer diameter about equal to the inner diameter of the hot die.

The portion of polymeric material removed from the inner surface along the necked tip can be removed by a rotary device. Additionally or alternatively, the portion of polymeric material removed from the inner surface along the necked tip can be removed by milling or laser ablation. The necked tip can be monitored to determine a removal depth, and the removing the portion of polymeric material from the inner surface along the necked tip can be terminated when the removal depth reaches a predetermined threshold.

Various suitable materials can be used. For example, the inner tubular member can include a material selected from the group consisting of nylon, polyurethane, polyethylene, co-polyamide such as Pebax (polyether block amide), polyester, or co-polyester. The inner tubular member can be a multilayer tubular member comprising a first layer, a second layer, and a third layer, further wherein the second layer is an outer layer relative to the first layer and the third layer is an outer layer relative to the second layer.

In some embodiments, the distal section of the inner tubular member is positioned in a balloon having a working length, a distal neck, and a distal leg, with the distal end of the inner tubular member extending distally beyond a distal end of the distal leg. The distal leg of the balloon can be coupled to at least a portion of the distal section of the inner tubular member.

Additionally, the balloon can include any suitable material, such as nylon, polyurethane, polyethylene, co-polyamide such as Pebax (polyether block amide), polyester, or co-polyester. For example, the balloon can be formed by melt-extruding a thermoplastic polymeric material to form a tube having a tube lumen and cooling the extruded tube to a temperature less than an elevated temperature of the melt-extrusion, placing the extruded tube within a capture member, and biaxially orienting the polymeric material of the extruded tube by radially expanding the extruded tube with pressurized media in the tube lumen and axially stretching the extruded tube with a load applied to at least one end of the tube.

As embodied herein, the balloon can be a multilayer balloon comprising a first layer and a second layer. The second layer can be an outer layer relative to the first layer. The first layer can include the first material having a first durometer hardness and the second layer can include second material having a second durometer hardness greater than the first durometer hardness. The first layer can include a first material having a first durometer between about 55D and about 63D. The first material can include polyether block amide. The second layer can include a second material having a durometer between about 70D and 72D. The second material can include polyether block amide.

A catheter having a monolithic distal tip is also provided. The catheter is prepared by a process including providing an inner tubular member formed from a first polymeric material. The inner tubular member has a distal section, a distal end, and a lumen defined therein by a first inner diameter. At least a portion of the distal section of the inner tubular member in necked down to form a necked tip having a second inner diameter. A portion of polymeric material is removed from an inner surface along the necked tip to define a third inner diameter for the necked tip. The catheter can include any of the features described herein for the method of fabricating a catheter. For example, the distal section of the inner tubular member can be positioned in a balloon having a working length, a distal neck, and a distal leg, with the distal end of the inner tubular member extending distally beyond a distal end of the distal leg. The distal leg of the balloon can be coupled to at least a portion of the distal section of the inner tubular member.

It is to be understood that both the foregoing general description and the following detailed description are exemplary and are intended to provide further explanation of the disclosed subject matter.

The accompanying drawings, which are incorporated in and constitute part of this specification, are included to illustrate and provide further understanding of the disclosed subject matter. It will be appreciated that the drawings are not to scale, and are provided for purposes of illustration only. Together with the description, the drawings serve to explain the principles of the disclosed subject matter.

DETAILED DESCRIPTION

Figure 1:
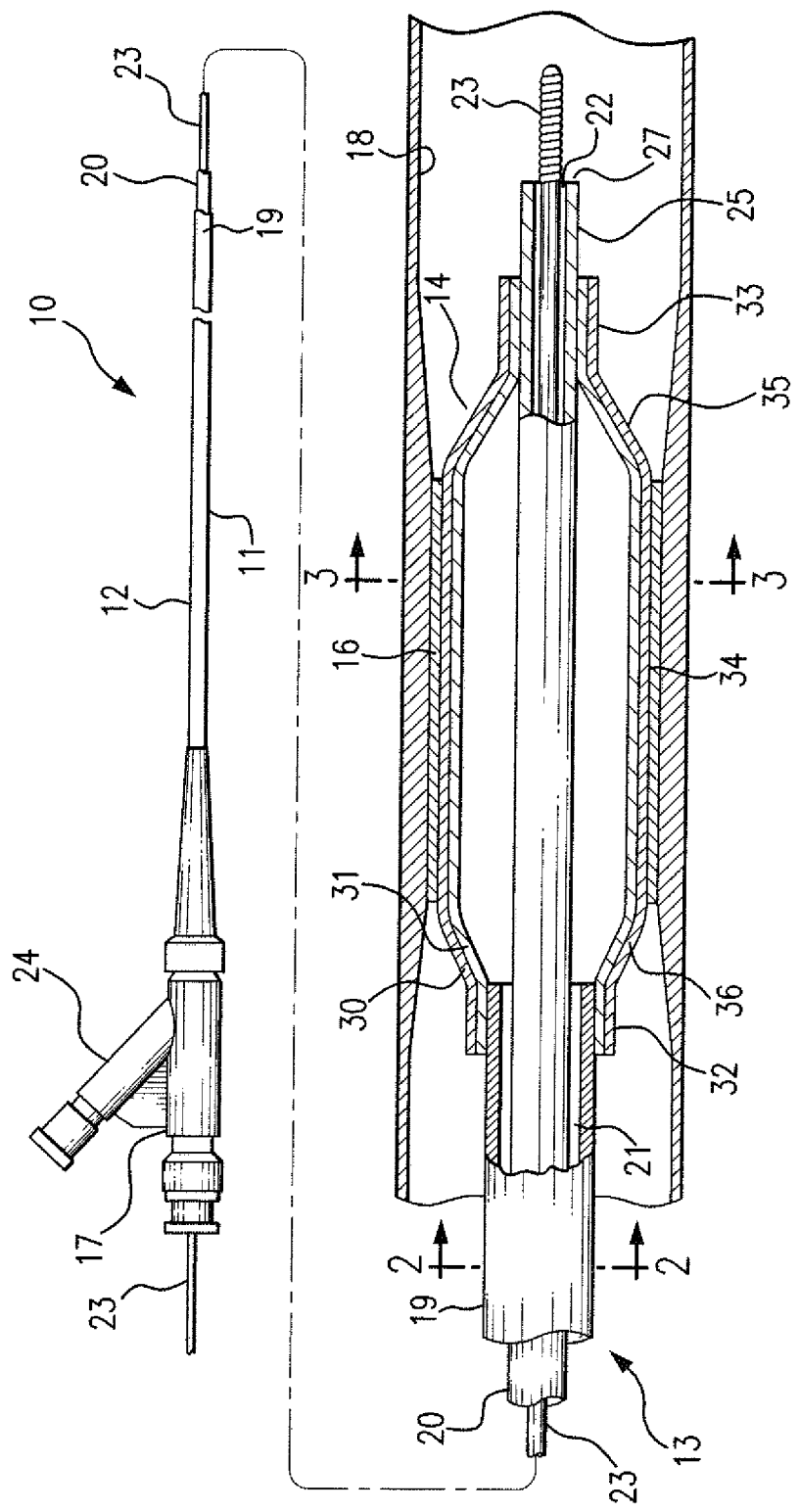
FIG. 1 schematically depicts a representative embodiment of a balloon catheter in accordance with certain aspects of the disclosed subject matter with the distal portion of the balloon catheter enlarged and in cross-section.

While the presently disclosed subject matter will be described with reference to a few specific embodiments, the description is illustrative of the disclosed subject matter and is not to be construed as limiting. Various modifications to the presently disclosed subject matter can be made to the preferred embodiments by those skilled in the art without departing from the true spirit and scope of the disclosed subject matter as defined by the appended claims. It will be noted here that for a better understanding, like components are designated by like reference numerals throughout the various figures.

In accordance with the disclosed subject matter, a method for fabricating a catheter is provided. The method includes providing an inner tubular member formed from a first polymeric material, the inner tubular member having a distal section, a distal end, and a lumen defined therein by a first inner diameter; necking down at least a portion of the distal section of the inner tubular member to form a necked tip having a second inner diameter; and removing a portion of polymeric material from an inner surface along the necked tip to define a third inner diameter for the necked tip. In some embodiments, the method includes positioning the distal section of the inner tubular member in a balloon having a working length, a distal neck, and a distal leg, with the distal end of the inner tubular member extending distally beyond a distal end of the distal leg; and coupling the distal leg of the balloon to at least a portion of the distal section of the inner tubular member.

Particular embodiments of this aspect of the disclosed subject matter are described below, with reference to the figures, for purposes of illustration, and not limitation. For purposes of clarity, the catheter and the method of fabricating the catheter are described concurrently and in conjunction with each other.

A representative balloon catheter produced according to the disclosed subject matter will now be described, for purposes of illustration and not limitation, with reference to FIGS. 1, 2, and 3. As shown in FIG. 1, a stent delivery balloon catheter 10 generally comprises an elongated catheter shaft 11 having a proximal shaft section 12, a distal shaft section 13, an inflation lumen 21, and a guidewire lumen 22 configured to slidably receive a guidewire 23 therein, and having a balloon 14 mounted on the distal shaft section. An adapter 17 on a proximal end of the catheter shaft can provide access to the guidewire lumen 22, and has an arm 24 configured for connecting to a source of inflation fluid (not shown). FIG. 1 illustrates the balloon in an inflated configuration within a patient's body lumen 18. A radially expandable stent 16 can be releasably mounted on the balloon 14 for delivery and deployment within the body lumen 18. The balloon catheter 10 can be advanced in the body lumen 18 with the balloon 14 in a noninflated configuration, and the balloon can be inflated by introducing inflation fluid into the balloon interior to expand the balloon 14 and stent 16 mounted thereon. The balloon 14 can then be deflated to allow for repositioning or removal of the catheter from the body lumen 18, leaving the stent 16 implanted in the body lumen 18.

Figure 2:
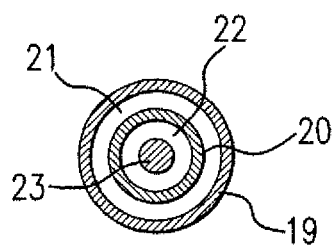
FIG. 2 is a transverse cross-sectional view of an embodiment of the catheter shaft along line 2-2.
Figure 3:
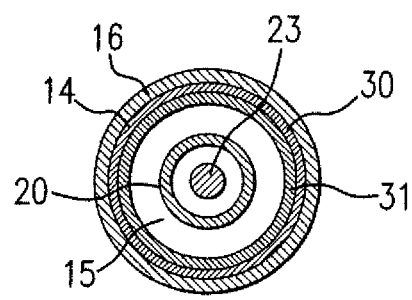
FIG. 3 is a transverse cross-sectional view of an embodiment of the balloon along line 3-3.

In accordance with one aspect of the disclosed subject matter, the shaft can comprise an outer tubular member 19 defining the inflation lumen 21, and an inner tubular member 20 defining the guidewire lumen 22 and positioned in the outer tubular member 19 such that the inflation lumen 21 is the annular space between the inner surface of the outer tubular member 19 and the outer surface of the inner tubular member 20, as best shown in FIG. 2 illustrating a transverse cross section of the catheter of FIG. 1, taken along line 2-2. The balloon 14 can have a proximal leg section 32 sealingly secured to the distal end section of the outer tubular member 19, and a distal leg section 33 sealingly secured to a distal section 25 of the inner tubular member 20, so that an interior 15 of the balloon is in fluid communication with the inflation lumen 21 of the shaft. FIG. 3 illustrates a transverse cross section of the balloon of FIG. 1, taken along line 3-3, with the patient's lumen omitted for ease of illustration.

Alternatively, although not shown, the shaft can be formed by an inner tubular member having two or more lumens defined therein, wherein at least one lumen forms an inflation lumen and another forms a guidewire lumen. Still further, the inner tubular member can be provided at the distal section of the catheter so as to form the guidewire lumen through the balloon, with the proximal end of the inner tubular member attached to the remaining proximal section of the shaft.

Figure 4:
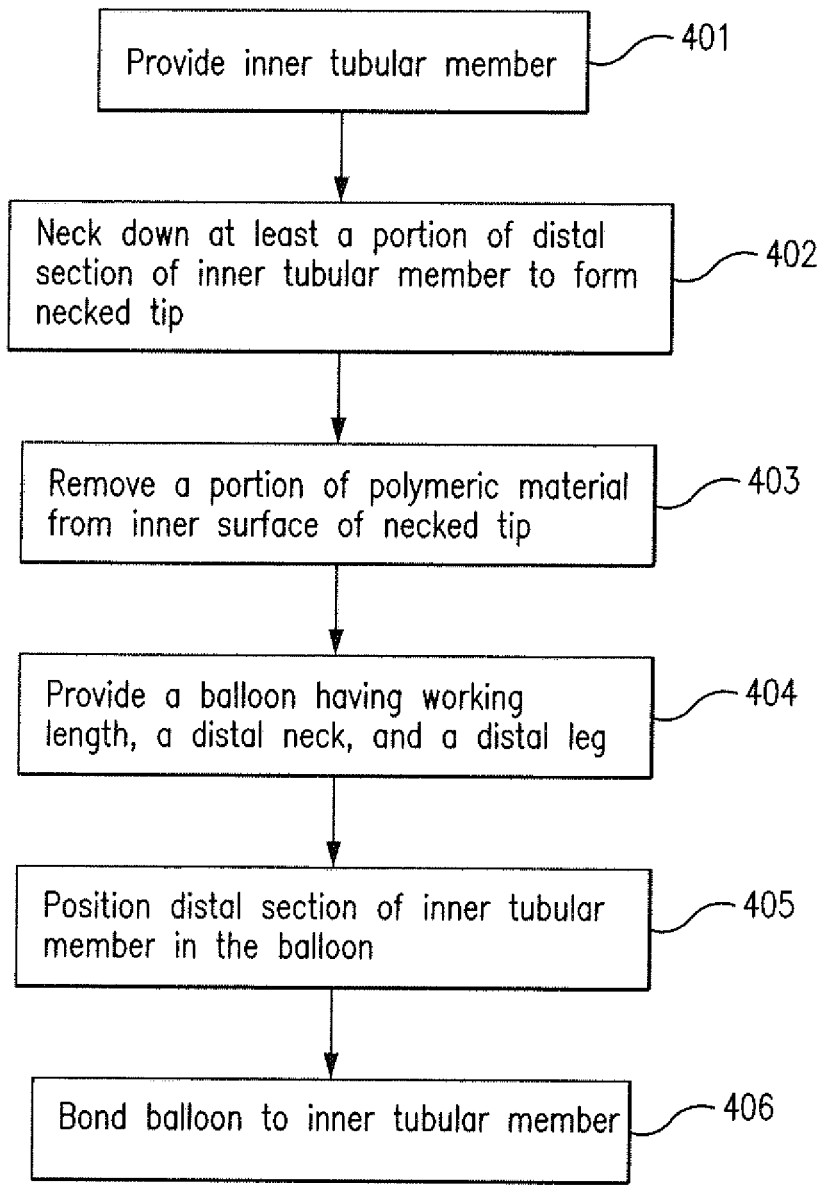
FIG. 4 is a flow diagram of a method of fabricating a balloon catheter according to some embodiments of the disclosed subject matter.

For the purpose of illustration and not limitation, FIG. 4 is a flow chart of an exemplary method of fabricating a balloon catheter in accordance with the disclosed subject matter. The method includes providing an inner tubular member 20 (401 in FIG. 4) formed from a first polymeric material and having a distal section 25, a distal end 27, and a lumen 22 defined therein by a first inner diameter. The inner tubular member 20 can comprise, for example, a single material of monolithic construction or a multi-layered tube. An example of a suitable multilayer tube includes a lubricious inner liner and bondable outer layer such as nylon or Pebax, or any of other suitable materials for the intended purpose. As embodied herein, the multilayer tube can include a first inner layer comprising a high density polyethylene (HDPE), a second intermediate layer comprising an adhesive layer, e.g., Primacor, and third outer layer comprising Pebax. Other examples of suitable materials are identified in U.S. Pat. Nos. 6,277,093 and 6,217,547, each of which is hereby incorporated by reference in its entirety. The inner tubular member 20 can be formed by conventional methods including but not limited to extrusion or coextrusion.

Figure 5:
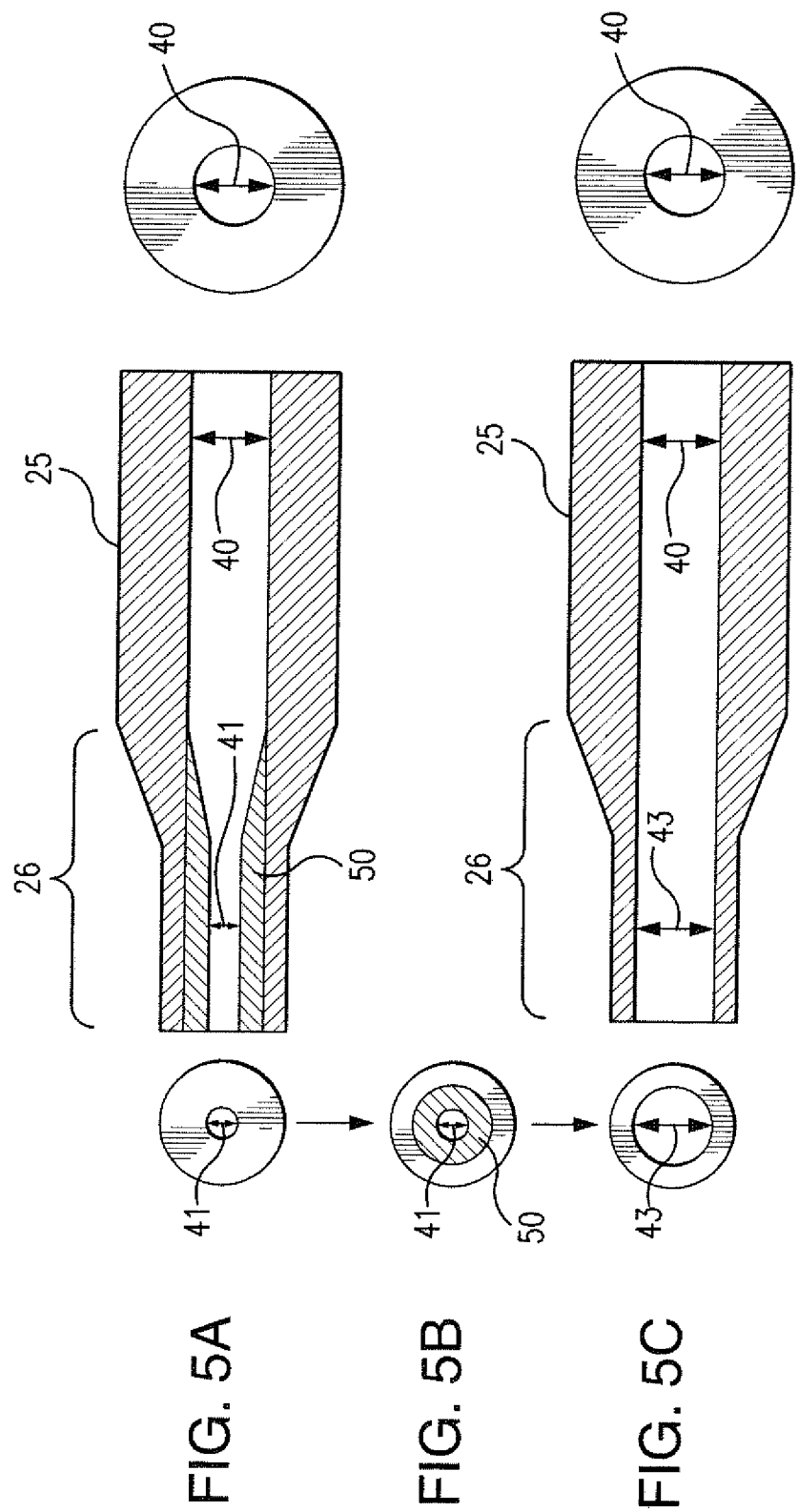
FIGS. 5A, 5B, and 5C are cross-sectional views of a schematic representation of a distal portion of an inner tubular member in accordance with the disclosed subject matter, wherein the distal direction is to the left as shown.

The method also includes necking down at least a portion of the distal section 25 of the inner tubular member 20 to form a necked tip 26 having a second inner diameter (402 in FIG. 4). For the purpose of illustration and not limitation, FIG. 5A illustrates the distal section 25 of inner tubular member 20 in accordance with one aspect of the disclosed subject matter. As depicted in FIG. 5A, at least a portion of the distal section 25 of the inner tubular 20 member can be necked down to form a necked tip 26. The inner tubular member 20 can have a first inner diameter 40 before necking, and after necking, the necked tip 26 can have a second inner diameter 41. As embodied herein, the second inner diameter 41 is less than first inner diameter 40 as shown in FIG. 5A.

A variety of suitable techniques can be used to neck down the tubular member. For example, the inner tubular member can be necked down by positioning a mandrel in the lumen 22 of the inner tubular member 20. The mandrel can, for example, have a stepped, tapered, or contoured shape such that the portion of the mandrel extending distally decreases in diameter. The stepped mandrel can have a first portion with a first outer diameter and a second portion having a second outer diameter, the second outer diameter forms the second inner diameter of necked tip 26. The first outer diameter of the mandrel can be selected to ensure the distal end of the inner tubular member is necked to a diameter to fit inside a necking die. As embodied herein, the larger second portion of the stepped mandrel can be positioned along the distal section 25 of the inner tubular member 20 that will form the necked tip 26 upon necking. In this manner, an outer diameter of the larger second portion of the mandrel is about equal to the second inner diameter 41 of the necked tip 26. Pre-necking thus can be performed, wherein the small end of the tapered mandrel can be used to stretch the inner member to fit in a hot die for necking. This pre-necked inner member portion can be trimmed off. The mandrel can be composed of a suitable material, such as metal (e.g., stainless steel or NiTi, coated or uncoated), ceramic, or the like. For example, the mandrel can be composed of Teflon coated or Paralene coated stainless steel which can allow ease of removal after assembly. A hot die can be used during necking such that the outer diameter of the necked tip is about equal to the inner diameter of the hot die.

The method of fabricating the balloon catheter also includes removing a portion of polymeric material from an inner surface along the necked tip 26 (403 in FIG. 4) such that the necked tip 26 has a third inner diameter. For the purpose of illustration and not limitation, FIGS. 5A, 5B, and 5C shows removing a portion of polymeric material 50 from an inner surface along the necked tip 26. For example, the portion of material 50 removed from the inner surface can be such that the third diameter 43 of the necked tip is about equal to the first diameter 40 of the inner tubular member 20. Accordingly, the inner tubular member can have a generally consistent inner diameter along its length for guidewire 23, yet a reduced outer diameter and amount of material at the necked tip 26 as shown in FIG. 5C. In this manner, a soft tip having a small entry profile with improved trackability and flexibility can be provided to prevent or minimize injury to a vessel during advancement within the tortuous anatomy of a patient's vascular, while maintaining the strength of the inner tubular member to prevent guidewire lumen collapse. In some embodiments, the method can also include removing a portion of polymeric material from an inner surface of the inner tubular member at locations proximal to the necked tip. For example, material can be removed from the section of the inner tubular member in contact with the distal leg 33 of the balloon 14, to form a generally consistent inner diameter along the lumen of the inner tubular member. Additionally or alternatively, the third diameter can be smaller than the first diameter to define a seal or the like to engage a guidewire position within the lumen. Alternatively, the third diameter can be larger than the first diameter to further reduce the material at the necked tip and thus increase flexibility.

Various suitable methods for removal of material are described in U.S. Pat. Nos. 7,967,836 and 8,292,913, each of which is hereby incorporated by reference in its entirety. In some embodiments of the presently disclosed subject matter, for example, a portion of polymeric material 50 (shown as cross-hatched portions of the necked tip 26 in FIGS. 5A and 5B) of the necked tip 26 can be removed by processing with laser or other thermal ablation process. Additionally or alternatively, a rotary device with support mandrel for the shaft can be used to rotate the necked tip. A high speed spindle with a milling or cutting bit can be used to remove at least a portion 50 of the necked tip 26.

In accordance with another aspect, a monitoring device, such as a gauge, caliper or a smart camera (not shown) can be used to monitor the shaft during the material removal process. The smart camera can, for example, monitor the necked tip 26 to determine and control a removal depth. The monitor device can be in communication to terminate removal of the portion 50 of the necked tip 26 when the removal depth reaches a predetermined threshold.

For purpose of fabricating a balloon catheter, the method also includes positioning the distal section of inner tubular member in a balloon having working length, a distal neck, and a distal leg (404 in FIG. 4). The inner tubular member can be positioned such that the distal section 25 of the inner tubular member extends distally beyond the distal end of the distal leg 33. Particularly, the necked tip of the distal section can be aligned with and/or extend from the distal end of the distal leg of the balloon.

As depicted in FIG. 1, for purpose of illustration and not limitation, a balloon 14 is disposed at a distal section 25 of the inner tubular member 20. The balloon includes an inner chamber 15 defined within a working length of the balloon, a distal neck 35 and a proximal neck 36. The interior chamber 15 of the balloon 14 is in fluid communication with the inflation lumen 21 extending the length of the catheter shaft 11. For example, and with reference to FIG. 2, the inflation lumen 21 can be defined as an annular space between the inner tubular member 20 and an outer tubular member 19 as generally known as a coaxial arrangement. Alternatively, the inflation lumen can be defined within the inner tubular member 20, such as a dual lumen configuration as is known in the art and noted above. As embodied herein, the inner tubular member 20 of the disclosed subject matter extends through at least a portion of the balloon. In this manner, and regardless of whether a dual lumen or a coaxial arrangement is provided, the necked tip of the distal section of the inner tubular member defines the distal tip of the catheter. With the inflation lumen coupled to the interior of the balloon, the balloon can be pressurized using any suitable fluid medium, including but not limited to water, contrast agents, or saline solution.

For purpose of illustration and not limitation, and with reference to a coronary balloon catheter, the length of the balloon catheter disclosed herein can generally be about 108 to about 200 centimeters, preferably about 135 to about 150 centimeters, and typically about 145 centimeters for PTCA, and can have other suitable dimensions for other various applications. The inner tubular member can have, for purpose of example and not limitation, an OD of about 0.43 mm to about 0.66 mm, and an ID of about 0.38 mm to about 0.46 mm depending on the diameter of the guidewire to be used with the catheter. For purpose of example and not limitation, the balloon can have a length of about 6 mm to about 100 mm, and an inflated working diameter of about 1.2 mm to about 30 mm.

In accordance with one aspect of the disclosed method, a balloon 14 can be formed with a working length 34, a distal neck 35, and a distal leg 33. The distal leg 33 can have a first segment with a first diameter and a first wall thickness. The distal leg can have a second segment with a second diameter and a second wall thickness. The second diameter can be greater than the first diameter and the second wall thickness is thinner than the first wall thickness as described in more detail in copending application Ser. No. 13/609,968, the contents of which is incorporated herein in its entirety. The balloon can have a proximal neck 36 and a proximal leg 32.

In some embodiments, the balloon 4 can be a multilayer balloon. For example, and as shown in FIG. 1, balloon 14 can include a first layer 31 and a second layer 30 which is an outer layer relative to the first layer 31. In the illustrated embodiment, the first layer 31 is on an inner surface of the second layer 30, with the second layer 30 defining an outer surface of the balloon 14 and the first layer 31 defining an inner surface of the balloon 14. However, balloon 14 can alternatively have one or more additional layers (not shown). Additional layer(s) can increase the dimensions of the tube/balloon formed therefrom to a desired value, and/or can be used to provide an inner or outer surface of the balloon with a desired characteristic. Therefore, it should be understood that the balloon 14 of the disclosed subject matter can have at least two layers, and can include one or more additional layers.

The balloon 14 can be composed of a wide variety of suitable materials, for example, nylon, co-polyamide such as Pebax (polyether block amide), polyester, co-polyester, polyurethane, polyethylene, or the like. More detailed lists of suitable materials are provided in U.S. Pat. Nos. 7,074,206, 7,828,766, and 8,052,638, each of which is hereby incorporated by reference in its entirety.

In some embodiments, the first layer 31 can be made of a first polymer material having a first durometer, and the second layer 30 can be made of a second polymer material having a second durometer. As embodied herein, the second durometer can be greater than the first durometer, and the second layer can be an outer layer relative to the first layer. For example and not limitation, the balloon embodied herein has a first layer 31 composed of Pebax having a durometer of between about 55D and about 63D. The second layer 30 can be composed of, for example, Pebax having a durometer of between about 70D and about 72D Pebax.

Although not illustrated, balloon 14 can have a noninflated configuration with wings wrapped around the balloon to form a low profile configuration for introduction and advancement within a patient's body lumen. As a result, the balloon inflates to a nominal working diameter by unfolding and filling the molded volume of the balloon.

For purpose of example and as embodied herein, the balloon 14 can be formed using a technique similar to that disclosed in U.S. Pat. Nos. 6,620,127, 7,828,766, 7,906,066 and 8,052,638, each of which is hereby incorporated by reference in its entirety. In some embodiments, the balloon 14 can be formed by melt-extruding a thermoplastic polymeric material to form a tube, then blow molding or forming in a mold into a blown balloon at a temperature less than an elevated temperature of the melt-extrusion under high pressure, for example between about 150 and about 500 psi. The blow molding can include placing the extruded tube within a mold or capture member. The extruded tube can be radially expanded under suitable conditions by introducing a pressurized fluid into the tube lumen until the outer surface of the extruded tube engages and conforms to the inner surface of the capture member. Furthermore, the polymeric material of the extruded tube can be biaxially oriented by axially expanding the extruded tube with a load applied on at least one end of the tube while radially stretching the extruded tube with a pressurized media in the tube lumen.

In accordance with another aspect, the balloon can be formed using a two stage blow mold process such as disclosed in U.S. Patent Publication No. 2012/0065718, which is hereby incorporated by reference in its entirety. When using the two stage blow mold process, for purposes of example and not limitation, the balloon can be blown initially in a first stage as disclosed in U.S. Patent Publication No. 2002/0065718.

In accordance with another aspect of the disclosed subject matter, the method of fabricating a catheter includes coupling the distal leg 33 of the balloon 14 to at least a portion of the distal section 25 of the inner tubular member 20 (405 in FIG. 4). For example and without limitation, electromagnetic energy, such as thermal, laser, or sonic energy, can be applied to the distal leg 33 of the balloon 14 to bond at least a portion of the distal leg 33 to the distal section 25 of the inner tubular member 20 and to reduce the second diameter of the distal leg 33. Heating the distal leg 33 of the balloon causes the polymeric material of the balloon 14 to soften, or melt and flow. In some embodiments, a heat shrink tubing (not shown) can be positioned around the outside of distal leg 33 of the balloon 14. The heat shrink tubing, also referred to as a "heat shrink sleeve", can be composed of a polymeric material configured to shrink when exposed to heat. U.S. Pat. No. 7,951,259, which is hereby incorporated by reference in its entirety, discloses the use of a heat shrink sleeve in fabricating a catheter with a flexible distal end. The heat shrink tubing, when heated, shrinks and exerts an inward radial force on the distal leg 33. With the polymer of the distal leg 33 in a molten or softened, the diameter of the distal leg 33 will be reduced by the force exerted by the heat shrink tubing. After the balloon is cooled, the heat shrink tubing can then be removed. Heating can be accomplished, for example, by laser heating (e.g., using a CO2 laser), contact heating (e.g., using aluminum nitride, resistance, RF), hot air, resistance heating, induction heating or the like. As embodied herein, for purposes of illustration and not limitation, a solid state laser can be used to heat the shrink tubing and soften the distal leg 33. As a result, the outer surface of the distal leg 33 can be tapered distally to a smaller outer diameter, while the distal leg 33, in its softened or molten state, can form a bond with the distal section 25 of the inner tubular member 20.

Figure 6:
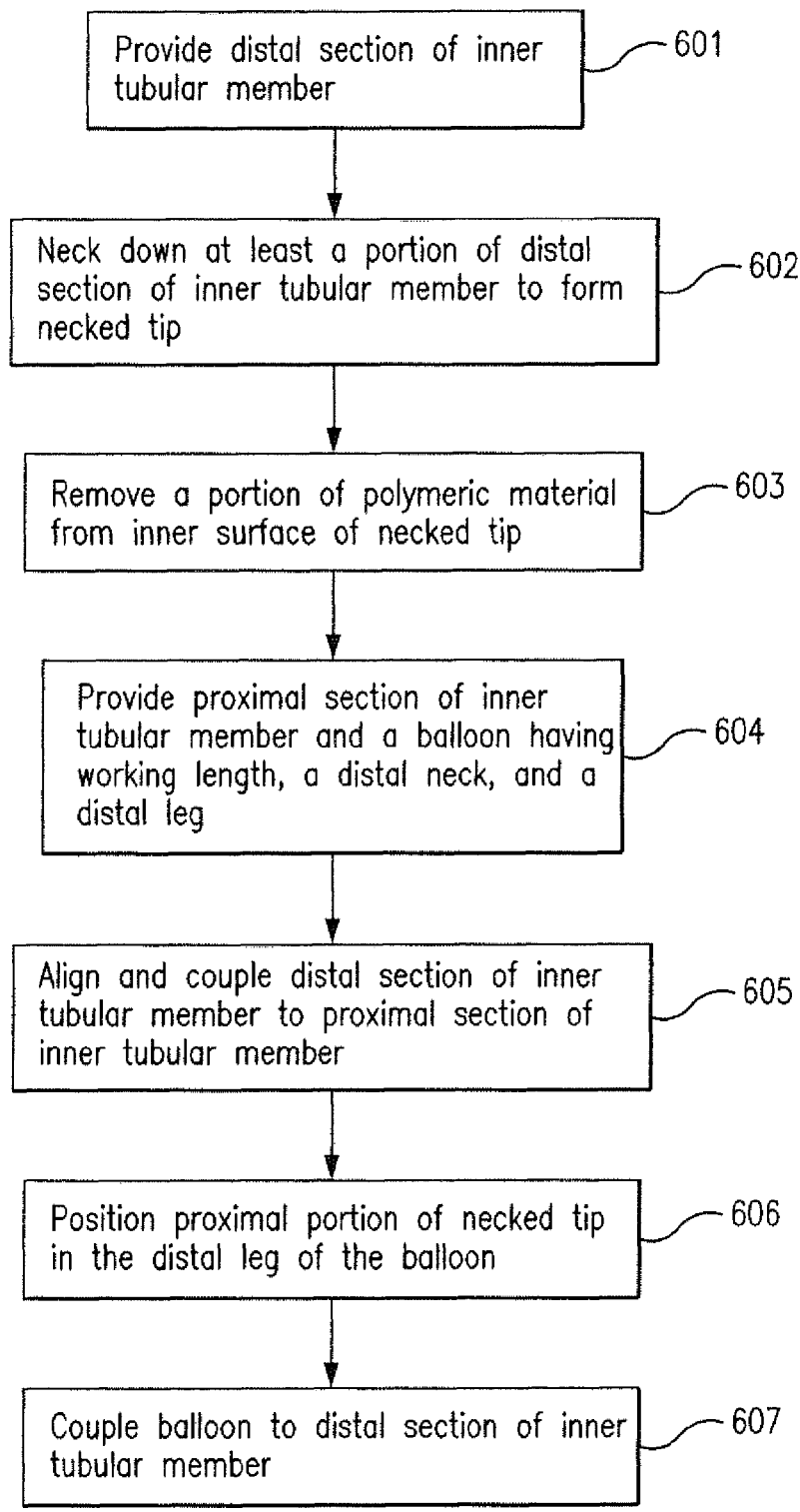
FIG. 6 is a flow diagram of a method of fabricating a balloon catheter according to some embodiments of the disclosed subject matter.

While FIG. 1 illustrates inner tubular member 20 as a single continuous member along its length including distal section 25 for purpose of example, alternatively, inner tubular member 20 can include two or more tubular member sections along its length. For example, distal section 25 of inner tubular member can be formed separately from a proximal section of inner tubular member. Distal section 25 can be bonded to proximal section of the inner tubular member at any suitable location along the length of the catheter (e.g., along the length of the balloon working section 34, distal neck 35, or distal leg 33) and by any means known to one of ordinary skill in the art such as a lap joint. Suitable connection means and locations are described in U.S. Pat. Nos. 8,403,885 and 8,657,782, each of which is incorporated by reference in its entirety. In such embodiments, the method of fabricating the balloon catheter can be modified as shown in FIG. 6, for the purpose of illustration and not limitation. The method includes providing distal section of the inner tubular member 601 and necking down at least a portion thereof to from a necked tip 602. A portion of polymeric material is removed from the inner surface of the necked tip at 603. The method also includes providing a proximal section of inner tubular member and a balloon having working length, a distal neck, and a distal leg 604, and aligning and coupling the distal section of the inner tubular member to the proximal section of the inner tubular member 605. The proximal portion of the necked tip is positioned in the distal leg of the balloon 606 and the balloon is coupled to the distal section of the inner tubular member 607.

Figure 7:
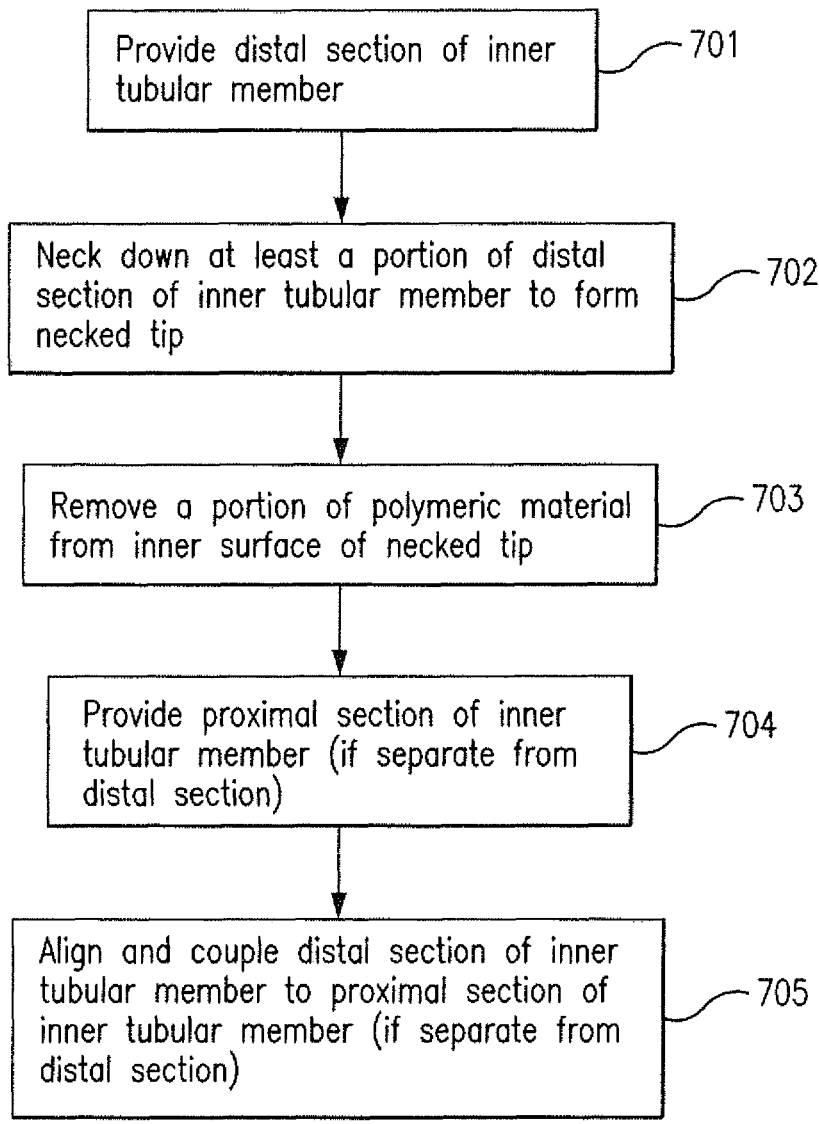
FIG. 7 is a flow diagram of a method of fabricating a stent delivery catheter having a retractable sheath according to some embodiments of the disclosed subject matter.

While the method of forming a catheter has been described above with respect to balloon catheters with or without a stent, the method can also be applied to other catheter devices known to one of ordinary skill in the art. For example, the methods described herein can be applied to catheters having a retractable sheath for delivery of a self-expandable stent. For the purpose of illustration and not limitation, FIG. 7 is a flow chart of an exemplary method of fabricating a stent delivery catheter having a retractable sheath in accordance with the disclosed subject matter. The method includes providing distal section of the inner tubular member 701 and necking down at least a portion thereof to from a necked tip 702. A portion of polymeric material is removed from the inner surface of the necked tip at 703. As described herein above, the inner tubular member can be a single member along the length of the catheter or can include two or more tubular member sections along its length. In embodiments having a tubular member with two or more sections, the method also includes providing a proximal section of inner tubular member 704 and aligning and coupling the distal section of the inner tubular member to the proximal section of the inner tubular member 705.

In accordance with some embodiments of the disclosed subject matter, the order of elements shown in FIGS. 4, 6, and 7 and described herein above can be changed and thus are not limiting. For example, the removing a portion of polymeric material from the inner surface of necked tip 403 in FIG. 4 can be performed after the bonding the balloon to the inner tubular member 406. Likewise in FIG. 6, the removing a portion of polymeric material from the inner surface of necked tip 603, can be performed after the distal section of the inner tubular member is coupled to the proximal section of the inner tubular member 605 or after the balloon is coupled to the distal section of the inner tubular member 607. For example, in some embodiments, the distal section of the inner tubular member can be so short and small that it can be difficult to remove material until after the distal section of the inner tubular member is bonded to other catheter components (e.g. the proximal section of the inner tubular member and/or the balloon). For FIG. 7, the removing a portion of polymeric material from the inner surface of necked tip 703, can be performed after the distal section of the inner tubular member is aligned and coupled to the proximal section of the inner tubular member 705

While the catheter illustrated in FIG. 1 is an over-the-wire catheter having an elongated inner tubular member 20 having a guidewire lumen 22 extending therein such that the guidewire 23 can extend from the adapter 17 through the lumen 22 and distally beyond a distal end of the catheter, other catheter arrangements are contemplated. For example, the guidewire lumen can extend along only a distal portion of the inner tubular member. Such a configuration is conventionally known as a rapid exchange balloon catheter, which generally includes a short guidewire lumen extending to the distal end of the shaft from a guidewire port located distal to the proximal end of the shaft. Additional suitable configurations and adaptations are disclosed in U.S. Pat. No. 8,052,638, which is hereby incorporated by reference in its entirety.

To the extent not previously discussed herein, the various catheter components can be formed and joined by conventional materials and methods. For example, inner tubular member can be formed by conventional techniques, such as disclosed in U.S. Pat. Nos. 6,277,093 and 6,217,547, each of which is incorporated by reference in its entirety. Additionally, although not illustrated, coiled or braided reinforcements can be included in the shaft at various locations, as is conventionally known as disclosed in U.S. Pat. No. 7,001,420, which is incorporated by reference in its entirety.

While the present disclosed subject matter has been described herein in terms of certain preferred embodiments, those skilled in the art will recognize that modifications and improvements can be made without departing from the scope of the disclosed subject matter. For example, although the catheter illustrated in FIG. 1 is an over-the-wire balloon catheter, the catheter in accordance with the disclosed subject matter can be a variety of suitable balloon catheters, including rapid exchange type balloon catheters having a guidewire proximal port located distal to the proximal end of the shaft, a guidewire distal port in the distal end of the shaft, and a relatively short guidewire lumen extending therebetween, or stent delivery catheters having a retractable sheath. While individual features of one embodiment of the disclosed subject matter may be discussed or shown in the drawings of the one embodiment and not in other embodiments, it should be apparent that individual features of one embodiment can be combined with one or more features of another embodiment or features from a plurality of embodiments.

The invention claimed is:

1. A method of fabricating a catheter, comprising:
    providing an inner tubular member formed from a first polymeric material, the inner tubular member having a distal section, a distal end, and a lumen defined therein by a first inner diameter;
    necking down at least a portion of the distal section of the inner tubular member to form a necked tip having a second inner diameter; and
    removing a portion of polymeric material from an inner surface along the necked tip to define a third inner diameter for the necked tip.

2. The method of claim 1, wherein the second inner diameter is less than the first inner diameter.

3. The method of claim 1, wherein the third inner diameter is about equal to the first inner diameter.

4. The method of claim 1, wherein the inner tubular member is necked down on a stepped mandrel having a first portion with a first outer diameter and a second portion having a second outer diameter, the second outer diameter being about equal to the second inner diameter.

5. The method of claim 1, wherein the tubular member is necked down using a hot die having an inner diameter, wherein the necked tip has an outer diameter about equal to the inner diameter of the hot die.

6. The method of claim 1, wherein the portion of polymeric material removed from the inner surface along the necked tip is removed by a rotary device.

7. The method of claim 1, wherein the portion of polymeric material removed from the inner surface along the necked tip is removed by milling or laser ablation.

8. The method of claim 1, further comprising monitoring the necked tip to determine a removal depth; and
    terminating removing the portion of polymeric material from the inner surface along the necked tip when the removal depth reaches a predetermined threshold.

9. The method of claim 1, wherein the polymeric material comprises a material selected from the group consisting of nylon, polyurethane, polyethylene, co-polyamide such as Pebax (polyether block amide), polyester, or co-polyester.

10. The method of claim 1, wherein the inner tubular member is a multilayer tubular member comprising a first layer, a second layer, and a third layer, further wherein the second layer is an outer layer relative to the first layer and the third layer is an outer layer relative to the second layer.

11. The method of claim 1, further comprising positioning the distal section of the inner tubular member in a balloon having a working length, a distal neck, and a distal leg, with the distal end of the inner tubular member extending distally beyond a distal end of the distal leg, and coupling the distal leg of the balloon to at least a portion of the distal section of the inner tubular member.

12. The method of claim 11, wherein the balloon comprises a material selected from the group consisting of nylon, polyurethane, polyethylene, co-polyamide such as Pebax (polyether block amide), polyester, or co-polyester.

13. The method of claim 11, further comprising forming the balloon by:
    melt-extruding a thermoplastic polymeric material to form a tube having a tube lumen and cooling the extruded tube to a temperature less than an elevated temperature of the melt-extrusion;
    placing the extruded tube within a capture member; and
    biaxially orienting the polymeric material of the extruded tube by radially expanding the extruded tube with pressurized media in the tube lumen and axially stretching the extruded tube with a load applied to at least one end of the tube.

14. The method of claim 11, wherein the balloon is a multilayer balloon comprising a first layer and a second layer, further wherein the second layer is an outer layer relative to the first layer.

15. The method of claim 14, wherein the first layer comprises a first material having a first durometer hardness and the second layer comprises a second material having a second durometer hardness, the second duromoter hardness being greater that the first durometer hardness.

16. The method of claim 14, wherein the first layer comprises a first material having a first durometer between about 55D and about 63D.

17. The method of claim 16, wherein the first material comprises polyether block amide.

18. The method of claim 14, wherein the second layer comprises a second material having a durometer between about 70D and 72D.

19. The method of claim 18, wherein the second material comprises polyether block amide.

* * * * *